United States Patent [19]

Lapeyre

[11] Patent Number: 4,588,404
[45] Date of Patent: May 13, 1986

[54] TOTAL CARDIAC PROSTHESIS

[76] Inventor: Didier Lapeyre, Chaignes, 27120 Pacy Sur Eure, France

[21] Appl. No.: 359,524

[22] Filed: Mar. 18, 1982

Related U.S. Application Data

[63] Continuation-in-part of Ser. No. 113,778, Jan. 21, 1980, abandoned.

[30] Foreign Application Priority Data

Jan. 22, 1979 [FR] France ............................ 79 01529
Nov. 29, 1979 [FR] France ............................ 79 29365

[51] Int. Cl.⁴ .............................................. A61F 2/22
[52] U.S. Cl. ...................................... 623/3; 128/1 D
[58] Field of Search .................... 3/1.7, 1; 128/1 D; 137/39; 623/3

[56] References Cited

U.S. PATENT DOCUMENTS

| | | | |
|---|---|---|---|
| 3,434,162 | 3/1969 | Wolfe | 3/1.7 |
| 3,536,423 | 10/1970 | Robinson | 3/1.7 X |
| 3,663,965 | 5/1972 | Lee, Jr. et al. | 3/1 C |
| 3,699,956 | 10/1972 | Kitrilakis et al. | 3/1 X |
| 3,766,567 | 10/1973 | Kahn et al. | 3/1.7 |
| 3,842,440 | 10/1974 | Karlson | 3/1.7 |
| 3,974,854 | 8/1976 | Kurpanek | 3/1.7 X |
| 4,222,127 | 9/1980 | Donachy et al. | 3/1.7 |

OTHER PUBLICATIONS

"Long-Term In Vivo Automatic Electronic Control of the Artificial Heart" by D. L. Landis et al, Trans. Am. Soc., Artificial Internal Organs, vol. XXIII, 1977, pp. 519-525.

Primary Examiner—Ronald L. Frinks
Attorney, Agent, or Firm—Browdy and Neimark

[57] ABSTRACT

The invention prosthesis is formed by a biventricular monoblock unit which comprises a sealed case implantable in the pericardial cavity. The actuating device is formed by two membranes working respectively by elongation and by deformation, and which constitute, with the corresponding internal face of the case, respectively, the right and left ventricular spaces having preferably the same volume but totally different geometry. The actuating device is associated with supplying apparatus which provide it with supply pressures subtantially equivalent to the physiological values of the ventricular pressures. The prosthesis is furthermore associated with a mechanism for regulating the cardiac flow.

26 Claims, 12 Drawing Figures

TOTAL CARDIAC PROSTHESIS

REFERENCE TO RELATED APPLICATION

This application is a continuation-in-part of my copending application Ser. No. 113,778, filed Jan. 21, 1980, and now abandoned.

BACKGROUND OF THE INVENTION

The present invention relates to a new "low profile" total heart prosthesis.

As it is known, heart diseases are the most important cause of death in human beings. The occlusion of the coronary arteries causes the ischaemia of the myocardium. The infarction of the myocardium may then cause a state of cardiogenic shock which requires, in an attempt to ensure the survival of the patient, the use of circulatory assistance means. Different solutions to this problem have been considered, among which may be cited heart transplants, the implantation of a partial cardiac prosthesis constituted by an auxiliary left ventricle and the total artificial cardiac prosthesis.

The problems posed by heart transplant are known: rarity of donors, histocompatibility, graft rejection and insufficiency of the answers provided by immunology to this rejection. It is these problems which up to now have not received satisfactory solutions, which have led research workers to consider substituting for a heart incapable of performing its function, an artificial organ which would not cause the immunological rejection reactions connected with heart grafts. Researchers turned then first to an auxiliary left ventricle prosthesis which would be implanted in association with the heart of the patient; though such a prosthesis may be considered valuable for remedying the failure of the left ventricle which is the most frequent origin of heart failures, it could not however remedy possible troubles of the existing parts of the diseased heart of the patient, since these latter would remain in place. The theoretically ideal solution would then be that represented by the radical replacement of the failing heart by a total cardiac prosthesis. A number of teams of research workers throughout the world, in the UNITED STATES, in the FEDERAL GERMAN REPUBLIC, in JAPAN, etc., particularly, are at present experimenting with cardiac prostheses on animals. These cardiac prostheses are double ventricular prostheses of the "membrane pump" type; they comprise a right ventricle and a left ventricle each activated independently by two separate sources of energy. Most of the cardiac prostheses at present presently being studied are designed to conform to the "principle of STARLING" according to which the variations of the blood flow induced by the circulatory network of the bearer of the prosthesis are obtained by variations of the volume of blood admitted into each ventricle under the effect of the variations of the atrial pressure, whereas the frequency of activation of the prosthesis is maintained constant. The cardiac prostheses proposed in the prior art are formed by a right ventricle and a left ventricle, independent of each other, both having identical design and volume in order to facilitate manufacture and implantation of the prosthesis. The independence of the two ventricles determines the existence therebetween of a relatively large anatomical dead space which reduces the physiologically usable volume and forms a prosthesis whose bulk is excessive, and having very poor fitting.

In addition, the construction of these prostheses in the form of two independent juxtaposed ventricles results in requiring the two ventricles to be activated independently of each other from independent sources of energy, which requires regulation between the two flows pumped by each one of the two independent prostheses. Furthermore, the design of known cardiac prostheses, in which the variations of the flow depend on the variations of the systolic volume due to the variations of the atrial pressure, requires a large diastolic reserve volume to comply with the variations of the needs of the organism. Thus, such a prosthesis, constructed with ventricular volumes corresponding to physiological requirements, may have difficulty in complying at the same time with the requirements of space determined by the dimensions of the pericardial cavity. Moreover, because of their relatively large volume and the relatively large space taken up, these double cardiac prostheses form to a certain extent an obstacle to the return circulation. Insofar as the volume and the space taken up by such prostheses are reduced, insufficient performances are obtained and consequently an insufficient blood flow when the needs of the organism increase (muscular exercise for example).

The aim of the present invention is therefore to provide a "low profile" new cardiac prosthesis which better answers the requirements of practice than the cardiac prostheses of the prior art, particularly in that it takes up less space than the prostheses proposed in the prior art, have a better fitting while permitting large flows, thus ensuring the same performances of that of the adult human non pathological heart. The invention uses optimally because of its small bulk, the physiologically usable volume of the pericardial cavity and practically eliminates any anatomical dead space. The invention requires a single source of activation for the right and left ventricles. The invention presents a functional geometry which approximates to the maximum the functional geometry of the natural right ventricle, thus promoting blood flow characteristics in the prosthesis and avoiding its coagulation; to thus avoid obstacles to venous return. The design of cardiac regulation output is based not only on the variations of the flow via variations of the systolic volume, but also on flow variations determined by the increase of the activation frequency of the prosthesis; and the invention takes into account not only "STARLING's Law" according to which the systolic volume depends on the atrial pressure, but also the Law of SARNOFF according to which the flow variations are accompanied by proportional variations of the force used (increase of power depending on needs).

SUMMARY OF THE INVENTION

The invention involves a one piece combined biventricular prosthesis. Volume displacement in the right ventricle is obtained by achieving variable elongation of a stiff large convex elastic membrane lying on a rigid support representing the interventricular septum. This rigid support has large fenestrations so that the membrane can be stretched by the variations of pressure in a common central pumping chamber. The support also prevents prolapse of the right membrane into the left side during diastole. The right ventricular chamber is bounded by this large convex septal wall and a concave free wall of the housing with a crescent shaped slit between them. Bellows action of the natural right ventrical is thus reproduced. Since the surface of the membrane is large and the space that separates it from the free wall is small, minimal motion of the elastic membrane towards the housing causes displacement of a large volume. Because the motion of the membrane is minimal, the mechanical stress imposed on the elastomer is compatible with long term functioning as demonstrated by current elastomer technology. Volume displacement in the left ventrical is obtained by deformation of a non-elastic membrane moving from one side to the other side of a symmetrical plane produced by a rigid support fixed inside the upper part of the concavity of the right rigid support.

The present invention provides a total cardiac prosthesis characterized in that it is essentially formed by a biventricular monoblock unit which comprises: a sealed case implantable in the pericardial cavity, made from a biocompatible material with respect to the surrounding tissues, and having a specific geometry which reproduces to the maximum the geometry of the natural heart; said case contains an actuating device formed essentially by two membranes one of which works by elongation and is separated from the corresponding internal face of the case by a space which delimits the right ventricle, and the second of which works by deformation and is mounted so as to define an interval, or left ventricular space, between it and the corresponding internal face of the case; means for isolating the prosthesis from the blood flowing in the ventricular spaces of the latter, mounted essentially respectively in association with the external face of the membrane which delimits the right ventricle and in association with the external face of the membrane which delimits the left ventricle; valves mounted in the valvular orifices provided in the case for anastomosis with the vessels of the circulatory network, which valves have a diameter compatible on the one hand with the auriculo-ventricular effective orifice area or surface area and the natural aortic pulmonary ejection characteristics and, on the other hand, with the kinetic pressures ejecting the blood circulating in the natural heart from the left ventricle into the aorta and from the right ventricle into the prosthesis, so as to avoid to the maximum loss of pressure phenomena and to reduce to a minimum the transvalvular pressure gradient; means for activating said actuating device associated with this latter and which provide it with supply pressures substantially equivalent to their physiological values; and means for regulating the heart flow as a function, on the one hand, of the filling pressure and, on the other hand, of the aortic pressure.

According to an advantageous embodiment of the cardiac prosthesis in accordance with the invention, the actuating device is formed by two membranes at least one of which is made from an appropriate elastomer material having specific high resistance to elongation, and each of which is supported by a supporting device made from a rigid material which cooperates therewith.

In accordance with an advantageous arrangement of this embodiment, the rigid material device supporting the membrane which works by elongation and which delimits the right ventricle is applied to the internal face of the said membrane, whose shape it closely assumes. This rigid device serves as a stop for this membrane at the end of the diastole.

In accordance with another advantageous arrangement of this embodiment, the volume of the left ventricular space and the volume of the right ventricular space are substantially equal, although of completely different geometry.

The "low profile" cardiac prosthesis of the present invention is advantageously activated by a single source of activation for the right and left ventricles ("monoactivated" option). It may however be convenient in some cases, particularly when the source of activation is pneumatic, to have in accordance with the invention two independent pumps acting respectively one on the elastic membrane of the right ventricle, and the other on the non elastic membrane of the left ventricle ("bi-activated" option).

It is quite important to note that in the case of the monoactivation right membrane is an elastic membrane having a low modulus of elasticity. In the case of bi-activation (two pumping chambers), the right membrane is an elastic membrane having a high modulus of elasticity.

According to another advantageous arrangement of this embodiment, in the case of "mono-activated" option, the rigid material device supporting the membrane which works by elongation has a plurality of through-apertures which provide communication between the gas and the membrane working by deformation, which defines the left ventricle.

According to yet another advantageous arrangement of this embodiment, the rigid material device supporting the membrane which works by deformation, supports said membrane laterally to allow its deformation within limits imposed by the presence of said supporting device.

In accordance with the present invention, the unit formed by these two membranes and their support devices forms a sealed unit itself housed in said sealed case, with which said unit is integrated by means of appropriate means provided in said case for receiving the ends of the two membranes and the ends of their respective supports. This central sealed unit can be thought of as the "heart" of the invention heart prosthesis. The unit performs all of the pumping function, the case serving as the means to define the walls of the chambers and the means to which to mount the valves, the blood bladders, etc.

According to a preferred embodiment of the cardiac prosthesis of the present invention, the distance between the membranes which delimit the left ventricle and the right ventricle and the corresponding internal face of said case increases in the three spatial dimensions from the tip towards the base of the prosthesis so as to orientate the speed vectors towards the corresponding valvular output orifice and to avoid any blood recirculation areas.

According to another advantageous embodiment of the cardiac prosthesis in accordance with the present invention, each of the valves mounted in the valvular orifices provided in the case is formed by a disk made from an appropriate hemocompatible material whose diameter is substantially identical to that of the valvular orifice in which it is mounted, which disk is inserted between an articulation bar and two stop bars which lock it in the open or closed position, in cooperation with said articulation bar, creating in the open position a maximum effective orifice area and offering minimum inertia and energy loss.

The invention uses separate blood bladders in each of the two chambers with the mouths of said bladders secured in place in the valvular orifices by the same means which mount the valves themselves in said orifices.

According to yet another advantageous embodiment of the cardiac prosthesis of the present invention, said case is equipped with inserts for quick connections to the bearer of the prosthesis, which inserts are mounted in valvular orifices provided in said case and are designed to receive respectively the securing end of the articulation bar and the securing ends of the stop bars, between which said valve is inserted.

In accordance with one form of the invention, the means for supplying the actuating device are formed by an implantable electro-pneumatic or electro-hydraulic energy converter whose energy provides the supply pressures required for said actuating device.

According to another arrangement of the invention, said means for supplying the actuating device are formed from a source of nuclear energy which provides the supply pressures required for said actuating device and are both implantable.

According to yet another arrangement of the invention, the means for supplying the actuating device are formed by an extra-corporal pneumatic energy source connected to the cardiac prosthesis by means of a small-diameter transcutaneous tube made from a material eliminating as much as possible the risks of transcutaneous infection.

As already said above, it may however be convenient in some cases, to have in accordance with the invention two independent pumps acting respectively one on the elastic membrane of the right ventricle, and the other on the deformable membrane of the left ventricle. In this particular arrangement of the embodiment, the rigid material support device for the membrane which works by elongation is pierced with only one gas supply opening.

In accordance with the present invention, the means for regulating the cardiac flow with respect on the one hand to the filling pressure and on the other hand to the aortic pressure are associated with means for supplying the actuating device and comprise a dual servo-control which serves to adapt the blood flow in the cardiac prosthesis to the variations of systemic resistances, on the one hand by regulating the activation pressure and the percentage of systolic time in the cycle to a reference value of the mean aortic pressure and, on the other hand, by regulating the duration of the activation cycle to the pressure in the left atrium between limits ranging between 700 to 430 milliseconds.

According to an advantageous arrangement of the invention, said means for regulating the cardiac flow comprise, in the case where they are associated with activation means formed by a pneumatic energy source: a first servo-control which comprises a mechanical device acting on a pressure reducer, which causes the activation pressure to vary between limit values of 150 to 250 mm Hg, under the action of a signal supplied by a comparator, after comparison of a signal corresponding to the effective aortic pressure of the bearer of the prosthesis, with a signal corresponding to a reference pressure, of 100 mm of Hg. If the effective pressure differs from the reference pressure, the pressure exerted on the stiff elastic membrane which delimits the right ventricle, increases or diminishes and the flow in said right ventricle varies correspondingly. A second servo-control which uses the increase of the flow in the right ventricle and the resulting increase in the mean pressure for filling the left atrium, which is represented by a pressure signal representative of the filling pressure of the left ventricle, is used to regulate the activation period between 700 to 430 milliseconds by means of a proportional signal supplied following the establishment, by a microprocessor, of a proportional relationship between the filling pressure of the left ventricle and the period of the activation cycle.

The regulation with respect to the aortic pressure is then achieved in accordance with the preceding arrangements by comparing a signal corresponding to the aortic pressure with a reference signal corresponding to the predetermined aortic pressure, for example 100 mm of Hg, the output signal from the comparator controlling the pressure of the fluid so as to cause the activation pressure to vary correspondingly on the elastic membrane of the right ventricle and consequently to cause the flow in this ventricle to vary. The choice of the reference signal, i.e. of the reference aortic pressure, corresponds to physiological circulating volume. Now, the circulating volume may vary depending on physiological conditions such as the feeding of the patient. In the case where drinks in particular are absorbed, the circulating volume increases and the aortic pressure of the normal heart increases so as to eliminate this excess of liquid by increasing perfusion through the kidneys.

This regulation of the circulating volume is a little-known characteristic of the heart, which it has seemed necessary to take into consideration so as to improve the regulation of the cardiac prosthesis of the present invention.

Consequently, according to another advantageous feature of the device for regulating the blood flow in accordance with the present invention, this device comprises a third servo-control for causing the aortic pressure reference level of the first servo-control to vary depending on the circulating volume, by detection of the mean filling pressure of the right ventricle and by comparison of this pressure with a reference pressure, the result of this comparison controlling the value of the specific reference pressure of the servo-control to the aortic pressure.

The variation of aortic pressure thus obtained corresponds to a small variation in the same direction of the filling pressure of the right ventricle.

According to another feature of the invention, to avoid accidental variations, the measurements of the mean right atrial pressure are stored for a predetermined period of time and it is the average of the stored measurements which is compared with the reference pressure.

According to another arrangement of the invention a variable-speed-gear-pump could be used in place of the pneumatic energy source.

The present invention also provides a process for regulating the blood flow in a cardiac prosthesis, by means of an electronic apparatus associated with mechanical means, which process is characterized in that it comprises a first servo-control which increases the blood flow by increasing the activation pressure exerted on the elastic membrane which delimits the right ventricle, and by increasing consequently the right systolic volume, and a second servo-control which uses the increase of flow in the right ventricle, which results in an increase of the mean atrial pressure in the left ventricle, to regulate the activation period, the two servo-controls acting synergetically. When the aortic pressure is insufficient, the first servo-control then increases the activation pressure, which causes the displacement of the volume in the right ventricle to increase, which determines in its turn an increase in the volume which reaches the left ventricle, which increases the filling pressure in the left ventricle. Picked up by the second servo-control, this allows the frequency to be regulated and the reproduction of SARNOFF's Law to be obtained according to which the increase in the activation frequency is tied to a proportional increase of developed force and increases the blood flow at the outlet of the prosthesis towards the aorta.

According to an advantageous embodiment of the process for regulating the blood flow in a cardiac prosthesis, said process comprises a third servo-control which causes the aortic pressure to vary depending on the variation of the volume of circulating blood, which results in a variation of the filling pressure of the right ventricle, whose measurement and comparison with a predetermined mean pressure control variation of physiological reference level of aortic pressure.

The present invention relates more particularly to cardiac prostheses conforming with the preceding arrangements, as well as to the means used for manufacturing and constructing same.

The prosthesis of this invention differs totally from the prior art in several regards and particularly by the fact that the geometry of the right ventricle differs completely from the geometry of the left ventricle, even though both ventricle volumes are preferably quite identical and by the fact that the displacements of volume into the ventricles are realized differently in the right ventricle and in the left ventricle: low elongation of a large elastic membrane at the right, and simple deformation of a non-elastic membrane at the left.

The invention prosthetic device reproduces the function of the natural heart very much closely in that its low bulkiness allows the suppression of any potential obstacle to the natural supply of the prosthesis and its performance (maximal potential flow-rate) is higher than those of known prosthesis.

An important advantage of the invention is that it fits well. "Fit" in this context means that the invention device closely approximates the anatomy of the human heart it replaces and because in its functioning it closely reproduces natural right ventricle blood ejection. The "fitting" problem is one of the most important unsolved problems of the prior art, and that problem is extremely well solved by the "low profile" total heart prosthesis, according to the invention.

The above and other objects, features and advantages of the present invention will become apparent from the following description, given solely by way of non-limiting illustration, when taken in conjunction with the accompanying drawings.

DESCRIPTION OF THE PREFERRED EMBODIMENTS

Figure 1:
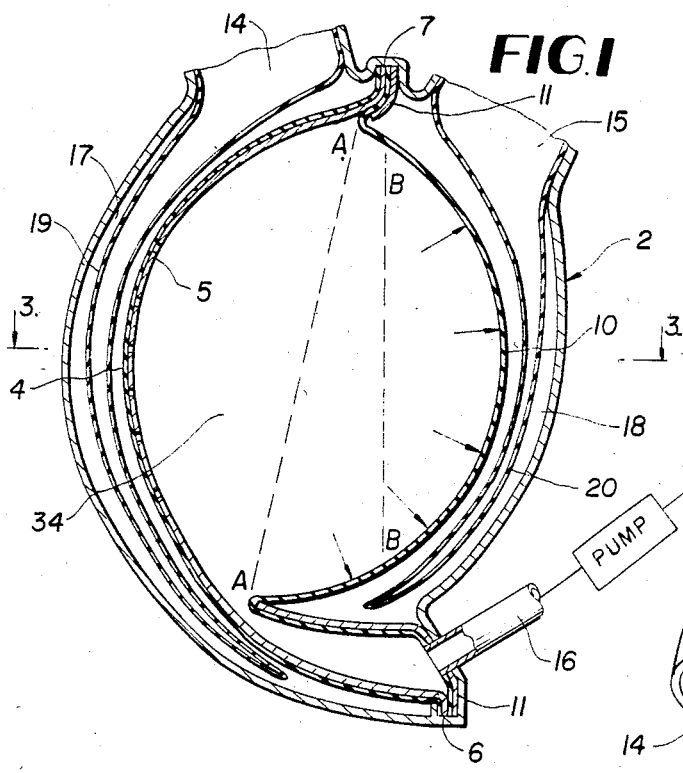
FIG. 1 is a longitudinal cross-sectional view of a cardiac prosthesis according to a first embodiment of the present invention.
Figure 1A:
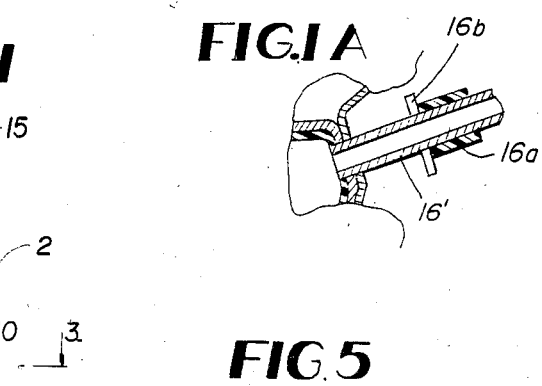
FIG. 1A is a detail of an embodiment of the invention.
Figure 5:
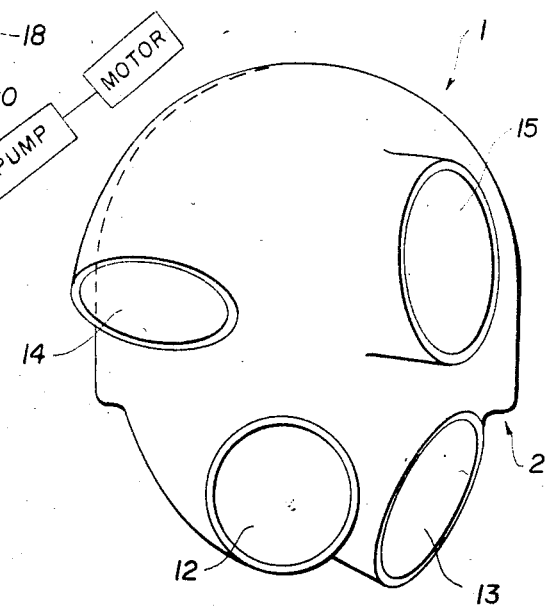
FIG. 5 is a schematic perspective view of the case of the prosthesis according to the invention comprising four valvular orifices.
Figure 2:
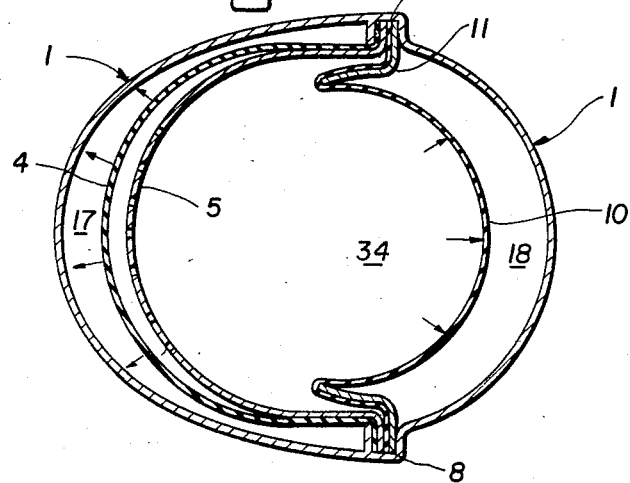
FIG. 2 is a cross-sectional view of the prosthesis taken along the line 3—3 of FIG. 1.

Referring to FIGS. 1 and 2, the complete cardiac prosthesis of the present invention is formed by a biventricular monoblock unit which comprises a case made from a biocompatible material with respect to the surrounding tissues, such as polyurethane, carbon or titanium for example. The case comprises an upper part 1 and a lower part 2 joined sealingly together by assembling by suitable fitting in the plane 3—3 for example, which is a plane perpendicular to the working directions of the actuating device which will be described further on. This case 1, 2 contains a membrane 4 made from an elastomer material which works by elongation and which has a large area, of the order of 80 to 110 $cm^2$ and which delimits the right ventricle of the prosthesis, with the internal face of the right-hand part of the wall of case 1, 2. The shape of membrane 4 is such that the right ventricular cavity widens out evenly in the three spatial dimensions, from the tip towards the base, when membrane 4 is put into an operational position. This elastomer membrane 4 presents specific elongation characteristics: the volume displaced varies from 80 to 150 ml when it is subjected to a pressure variation of 150 to 250 mm Hg. This membrane 4 is supported by a support device 5 formed by a plate of rigid material such as stainless steel for example, which assumes the exact shape of membrane 4 which is applied to the external face of support device 5. This latter is fixed to case 1, 2, conjointly with membrane 4, in a housing 6, 7, 8, 9 of the case (cf. FIG. 2), provided for this purpose, which extends over the whole height of the prosthesis, from the tip to the base thereof. Plate 5 is advantageously pierced with holes over the whole of its surface to ensure the communication of gas distributed by a pneumatic energy source connected to the prosthesis with the membrane which delimits the left ventricle. The gas may be air, helium or nitrogen, for example. A second membrane 10 is also mounted in case 1, 2; this membrane 10 which delimits the left ventricle with the internal face of the left-hand part of case 1, 2 works by deformation (and not by elongation like membrane 4) on each side of a plane AA which forms a specific angle—between 4° to 9° (presently 6°) with the longitudinal axial plane BB of the prosthesis in order to get the maximum ejection fraction without membrane 10 contacting the internal side of the case 2. For that, membrane 10 is fixed laterally to a rigid material support 11 such as a stainless steel for example, and support 11 with the corresponding part of membrane 10 are fixed in corresponding housings 6, 7, 8, 9 of case 1, 2. Valvular orifices (cf. FIG. 5) 12, 13, 14 and 15 are provided in case 1, 2, which is connected by means of a connection generally shown by reference numerals 60 and 16 in FIGS. 1, 3 and 4 to a pneumatic energy source 62 through a tube of small diameter when the pneumatic energy source is not implanted. The tube is covered with reinhabitable tissue and comprises at its end a carbon pyrolyte disk 16b placed under the skin 16a as shown in FIG. 1A, which prevents axial shearing of the tube 16' on the skin and avoids infections.

The mounting of membranes 4 and 10 in case 1, 2 is such that the right ventricular space 17 which separates membrane 4 from the internal face of the right-hand wall of case 1, 2 increases in the three spatial dimensions from the tip to the base of the prosthesis. Similarly, space 18 which separates membrane 10 from the internal face of the left-hand wall of case 1, 2 also increases in the three spatial dimensions from the tip to the base of the prosthesis. Such an arrangement results in promoting the laminar flows without turbulence and eliminating the zones of zero speed in the ventricular spaces 17 and 18 while orientating in ventricular spaces 17 and 18 the speed vectors of the blood towards the output, i.e. towards the aorta and the pulmonary artery, respectively. A thin blood bladder 19, 20 (see FIGS. 1 and 7 and the description below) made from a hemocompatible material (anti-thrombogenic material), such as polysegmented polyurethane for example, isolates the actuating device formed by membranes 4 and 10 and the case from the blood circulating in ventricles 17, 18 of the prosthesis of the invention. The volumes of the right 17 and the left 18 ventricles are substantially equal and are respectively of the order of 150 cm$^3$. Right ventricular volume is preferably quite identical to left ventricular volume although geometry of each ventricle being totally different.

Figure 3:
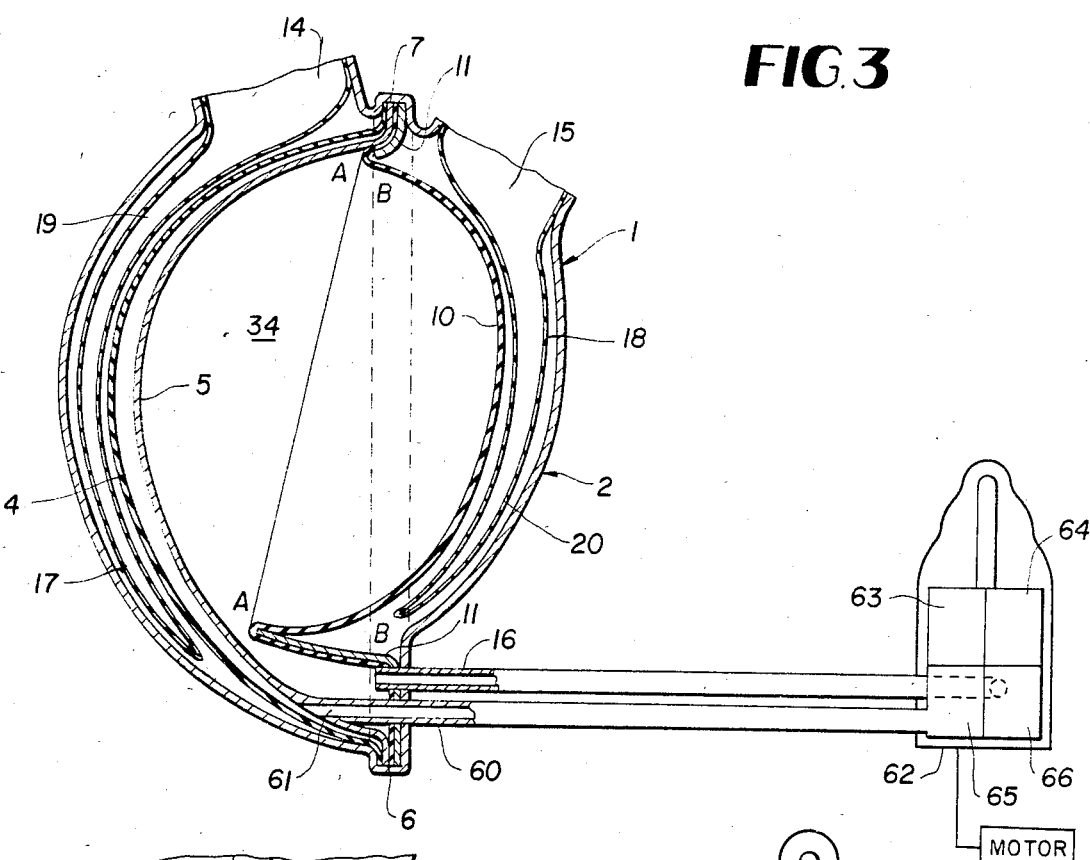
FIG. 3 is a view like FIG. 1, showing a biactivated embodiment.
Figure 4:
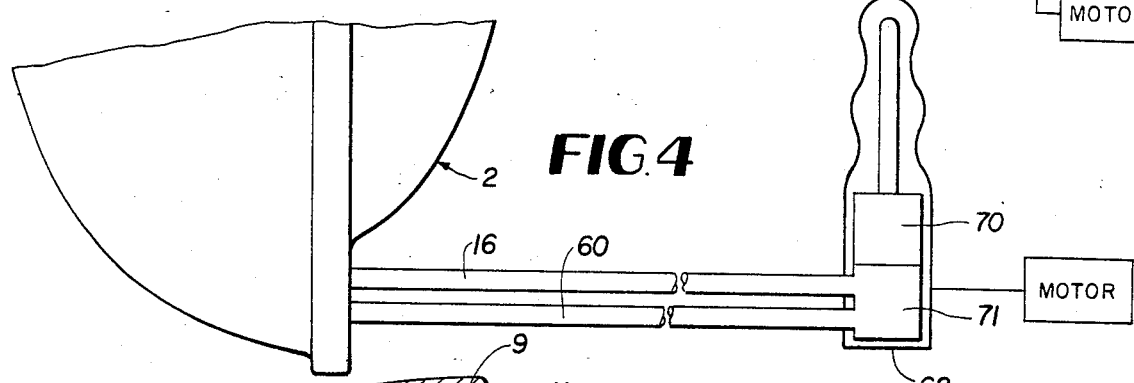
FIG. 4 is also a longitudinal sectional view of another biactivated embodiment.

FIGS. 3 and 4 also show some of the versatility of the invention as to the manner in which it operates biactively. In this case, rigid support of wall 5 has no openings except at the level of the end of pipe 60.

FIG. 3 shows an energizing module 62 having dual pumping chambers or pumps 63 and 64 which are associated with connection and regulation units 65 and 66, respectively. Pipes 60 and 16 respectively connect the units 65 and 66 to the two chambers of the invention heart prosthesis.

In FIG. 4, a single pump 70 with power sufficient to activate the left ventricle feeds alternatively both ventricles through a connection and regulation unit 71. The energy for releasing the elastic membrane 4, during the diastole of the right ventricle, is recovered at the entry of the pump during the systole activation of the left ventricle. The systoles of both ventricles are spaced by about ½ of a time of one cardiac beat.

In the case of the mono-activated option, the energizing module 62 provides pneumatic energy between the rigid wall 5 and the membrane 10 to thus operate both ventricles of the heart. The wall 5 allows this energy to flow through to operate the membrane 4 because of the openings in this wall 5.

The pump, of whatever form, with its connection unit, is servo-controlled by signals emitted by the three different modes of servo-control described below. The control signals to both ventricles are in synchronization, that is at the same frequency. The systoles to both the right and left ventricles can be provided at the same moment, that is, in phase. In the case of biactivated option as the durations of the systoles are shorter than the durations of the diastoles, for each ventricle, it is possible by making the systole of one ventricle during the diastole of the other one, or vice a versa, to optimise the efficiency of the energizing module 62.

The systoles of the right and left ventricles are always operated in synchronization, but they can be operated either in or out of phase. The activation in phase is shown by the apparatus of FIG. 3, whereas activation in opposition of phase can be accomplished by the alternate structure of FIG. 4.

The invention provides improved valve means, and improved means to mount the valves together with the blood bladders on the case.

To this end, referring to FIGS. 6, 7 and 8, inserts shown generally by the reference numeral 23, are mounted in the case 1 and more specifically in valvular orifices 12, 13, 14, 15 which are respectively the aortic, mitral, pulmonary and triscupid orifices, a little below the plane of the mouth of said orifices.

Figure 7:
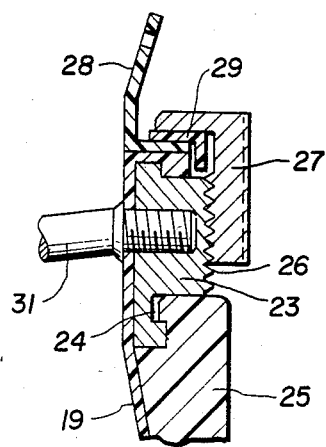
FIG. 7 is an enlarged cross-sectional view of the right hand upper corner of the FIG. 6.
Figure 8:
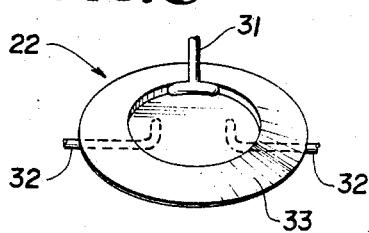
FIG. 8 is a front somewhat schematic and somewhat perspective view of a valve in accordance with the invention.

These inserts 23, one of which is shown on an enlarged scale in FIG. 7, are parts which form the junction between the cardiac prosthesis and the bearer of the prosthesis, and which allow valves 22 of the invention to be placed in the valvular orifices in a way which considerably reduces pressure drops (since internal diameters are large). Insert 23 comprises a body made from stainless steel for example. A housing 24 for the insert has force-fitted therein a corresponding section 25 of the edge of the valvular orifice 12, 13, 14 or 15 which receives the insert, this section mating with said housing 24. Insert 23 comprises furthermore a thread 26 which receives a junction piece 27 which holds tight through the use of a ring 29 and a "Teflon" collar 28 for anastomosis to the bearer of the prosthesis. As shown in FIG. 7, the lip of the blood bladder 19 is sealed to the valvular orifices by "pinching" between insert 23 and parts 28 and 29, and is secured in place by junction piece 27. Thus, the blood bladders 19 and 20 are secured at the valvular orifices only and otherwise are free in the heart chambers. The blood bladders are sized so as to be able to completely fill their respective chambers.

Insert 23 bears furthermore the articulation bar 31 of a valve generally designated by the reference numeral 22 and the two stop bars 31 and 32 of said valve; disk 33 of the valve, which forms the valve properly speaking, is inserted between free ends of bars 31 and 32. It is formed preferably of an appropriate hemocompatible thermoplastic material; its diameter is substantially identical to that of the valvular orifices with which it is associated and is also substantially identical to that of the vessels to which the prosthesis is to be anastomosed. Because of the fitting of the ends of the bars of valve 22 into inserts 23 and elimination of the metal support ring with which prior Art known valves are provided, the causes of flow restriction (pressure drops) are eliminated to a large extent as well as, to a considerable extent, the causes of thrombogenesis (since the internal diameter of the valve is so larger).

Figure 6:
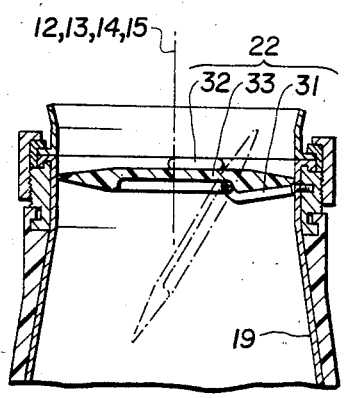
FIG. 6 is an axial cross-sectional view through a valvular orifice with the blood bladder in place and showing the valve in the closed position in solid lines and in the open position in mixed dash-lines.

FIG. 6 refers to valves which are mounted on triscupid and mitral orifices. Of course, the valves are mounted inversely on aortic and pulmonary orifices. In such cases, valves 22 open towards the artery (aorta or pulmonary artery). The valves in all positions operate automatically by the pumping pressure on the blood and due to the blood flow.

In use, the volume displacements in the right ventricle are obtained by causing to a greater or lesser degree, under the action of the compressed gas from the pneumatic distributor, the elongation of the convex elastic membrane 4, which represents the interventricular septum of the natural heart. Because of the large area of membrane 4 and because maximal elongation of the elastomer used is high (>600%), the effective amplitude is small and the mechanical stresses imposed on the elastomer which forms membrane 4 are negligible, inasmuch as the elastomer which forms membrane 4, which works by periodic stretching, is only subjected to an elongation of the order of 7–20% because of the large area of the membrane, so that the fatigue to which it is subjected is practically zero. The volume displacements in the left ventricle are obtained by deformation of the non-elastic membrane 10, on each side of the plane AA of the prosthesis.

A cardiac prosthesis must pump all the blood which reaches it from the circulatory network without the mean supply pressures of the ventricles deviating from their physiological values which are from $-2$ to $+7$ mm of Hg for the right ventricle and from $+5$ to $+15$ for the left ventricle.

Since the blood flow which reaches the heart is inversely proportional to the value of the resistances of the systemic area, the flow pumped by the heart in this area must also be inversely proportional to these resistances in order to maintain the arterial pressure at its physiological value.

For this, with an adult subject of 80 kg, the sensitivity of the left ventricle to the filling pressure must be of the order of 1.3 liter per mm of Hg and per minute, which in practice corresponds to flow variations of the order of 4 to 17 liters per minute.

To reproduce with a cardiac prosthesis the performance of the natural heart when the organism goes over from rest conditions (oxygen consumption $\simeq 300$ cm$^3$/minute) to those of muscular exercise of maximum intensity (oxygen consumption 1500 cm$^3$/minute), three types of adaptation are possible. A flow adaptation based only on the variations of the systolic volume under the effect of the variations of the filling pressure; a flow adapation based on the frequency variations; a flow adaptation comprising, like the natural heart, these two mechanisms brought into play in a synergistic fashion.

A self-regulation of flow based solely on the variations of the systolic volume such as is provided at the present time with most known prostheses is insufficient for the following reason: the frequency usable in practice over an extended period is from 70 to 110 cycles per minute; the self-regulation of flow involves then a large diastolic reserve volume which is not compatible with the anatomical constraints. Moreover, the inlet valves used up to now do not exceed an internal diameter of 30 mm. Since the time required for ejecting the volume of blood contained in the ventricle is from 35 to 40% of the cycle, the time left free for filling in the cycle is only of the order of 300 to 425 milliseconds. Now the maximum volume of blood which can pass during this time from left atrium into the ventricle when the mean filling pressure is at its highest acceptable level (15 mm of Hg) is under these conditions only from 110 to 130 ml (filling impedance).

The factors limiting the flow when operating at a fixed frequency are then on the one hand the anatomical constraints which limit the available reserve volume and, on the other hand, the pressure drops at the level of the inlet valve which limit the use of this volume.

In practice, for an effective overall bulk greater than 600 cm$^3$, known prostheses of the prior art provide at a filling pressure of 15 mm of Hg a maximal flow less than 13 liters/minute.

Other investigators have attempted to achieve flow regulation by means of appropriate frequency variations. These prostheses operate with a constant systolic volume, an electronic device stopping the filling phase as soon as the ventricles are full, under the effect of a contact signal. Since these prostheses are made in two independent parts, right and left, the space taken up limits the maximum systolic volume to 100 ml.

It has become obvious that the assoication, in accordance with the invention, of a monoblock prosthesis of small bulk (400 cm$^3$), having large reserve volumes (155 ml), large inlet valves (35 mm internal diameter) with a regulation device related at one and the same time to the variations of the systolic volume (STARLING), to the frequency and to the ejection power (SARNOFF) allows more extensive flow variations to be covered while complying with the physiological filling pressure indicated above and, consequently, ensures better regulation of the arterial pressure. In accordance with the invention such a device controls the duration of the filling phase with respect to the filling pressure of the left ventricle and the activation pressure with respect to the resistances of the systemic part of the cardiovascular circuitry.

In accordance with the invention, this regulation device comprises two servo-controls, namely:

A first servo-control (see FIG. 9) establishes a relationship between, on the one hand, the activation pressure used on the pneumatic pressure distributor and the percentage of the pressurizing time during the cycle and, on the other hand, a reference value of the mean aortic pressure. The mean aortic pressure taken as reference is that of the patient before implantation of the prosthesis, i.e. 90 to 120 mm of Hg. The effective mean aortic pressure is detected by morphological analysis of the curve of the rise in pressure of the air collected in the activation tube, as near as possible to the prosthesis (cf. "pneumo cardiogram"). This curve allows the following to be determined: (1) the opening of the outlet valve of the left ventricle and the corresponding pressure, which is the diastolic pressure of the subject; (2) from the detachment point corresponding to the opening of said valve, the pressure curve bends and corresponds to ejection of the whole contents of the left ventricle into the aorta; the apex of this phase corresponds to the "systolic" pressure of the subject; (3) the curve then straightens up again to reach the pressure value used on the pneumatic pressure distributor.

Since the activation membrane 10 of the left ventricle is not elastic, the slope of the curve from the third detachment point depends only on the resistance of membrane 4 of the right ventricle to elongation, since the activation pressure is common to the right and left ventricles. The morphological analysis of the activation pressure curve enables the diastolic pressure and the systolic pressure of the subject to be determined. From this signal the mean aortic pressure is taken: this signal controls: the activation pressure between limit values of 150 to 250 mm Hg, the percentage of the systole time in the activation cycle between the limit values of 33% to 43%. If the mean aortic pressure measured is greater or smaller than the value chosen as reference, the activation pressure must increase or diminish in the reverse direction. The percentage of systole time in the cycle must increase or diminish in a reverse direction. Variation of the mean aortic pressure above or below the reference value causes then a variation in the reverse direction of the activation pressure and of the percentage of the systole time in the cycle within the limits indicated above. This results in an increase or a reduction in the volume displaced by the right ventricle and so the supply flow of the left ventricle.

This first servo-control effects then three operations: (1) extraction of the control signal from the pressure rise curve of the air; (2) processing of this signal to modulate the percentage of pressurizing time in the cycle within the limit values of 33 to 43%; (3) actuation of a mechanical device acting on a pressure reducer associated with the pneumatic pressure distributor to regulate the pressure in module 62, of said distributor between 150 to 250 mm Hg; depending on the mean aortic pressure measured on the subject. The purpose of changing the systolic/diastolic ratio is to maintain the duration of the systole above the minimum value (210 milliseconds ±10%) required for ejection of the whole volume contained in the ventricles.

Figure 9:
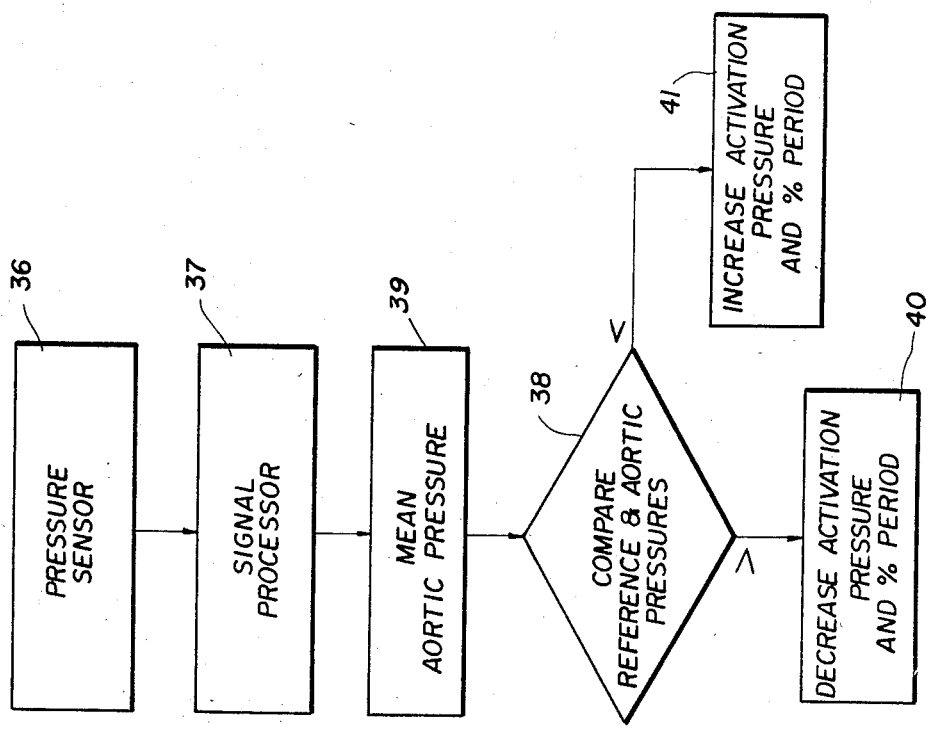

According to the diagram shown in FIG. 9, the first servo-control comprises a pressure sensor 36 on the activation pipe 16, an electronic device 37 for processing the signal supplied by sensor 36, through the morphological study of the pressure rise curve of the gas, a comparator 38 which picks up the signal corresponding to the mean aortic pressure 39 of the bearer of the prosthesis and compares it with the signal corresponding to the predetermined reference aortic pressure and provides a signal for adjusting the activation pressure and the systolic/diastolic ratio: if the mean effective aortic pressure 39 compared by device 38 is greater than the predetermined reference aortic pressure, the signal supplied at 40 causes, a reduction of the activation pressure and reduction of systolic/diastolic ratio. If the mean effective aortic pressure 39 compared by device 38 is less than the reference aortic pressure, the signal supplied at 41 causes, an increase of the activation pressure and systolic/diastolic ratio.

A second servo-control (see FIG. 10) establishes a relationship between the period of the activation cycle and the filling pressure of the left ventricle.

To a mean filling pressure of the left ventricle of 6 mm Hg there corresponds a frequency of 95 cycles per minute (630 milliseconds). An increase in the mean filling pressure of the left ventricle above 6 mm Hg determines a reduction in the duration of the cycle up to a limit value of 430 milliseconds and a reduction in the mean filling pressure of the left ventricle below 6 mm Hg determines an increase in the duration of the cycle up to a limit value of 700 milliseconds.

This second servo-control functions to convert the pressure signal obtained into a time signal.

Figure 10:
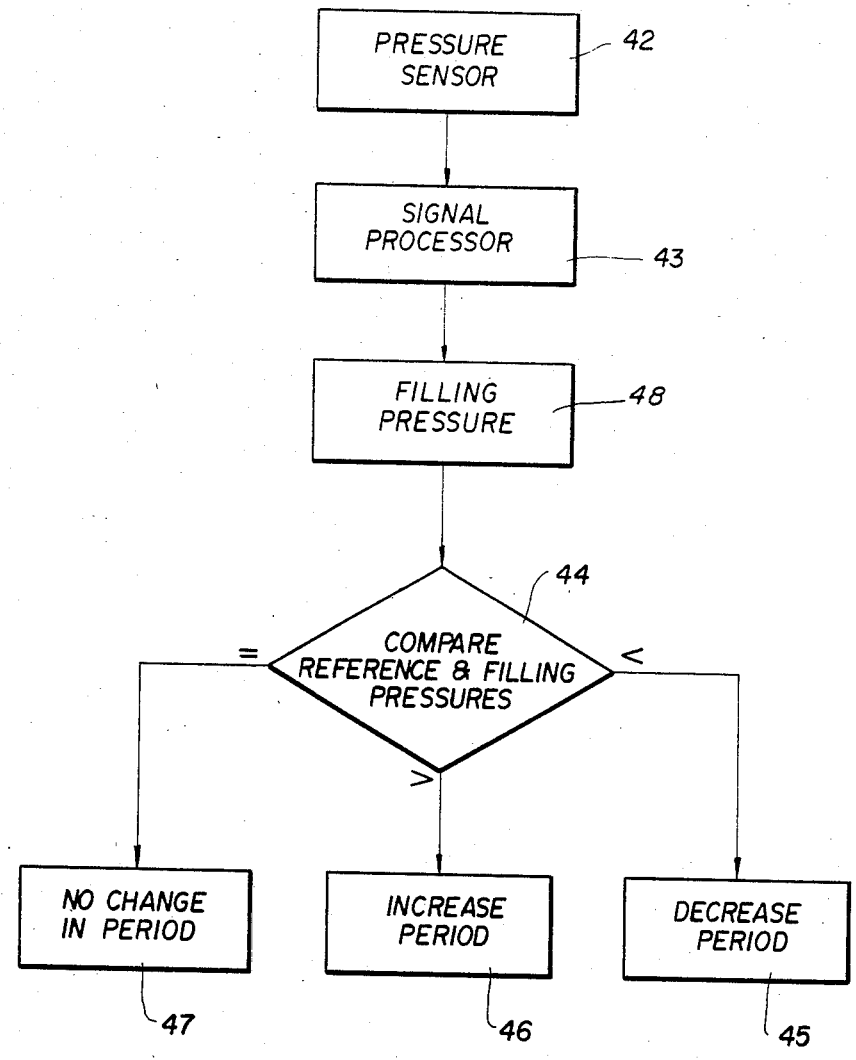

In accordance with the diagram shown in FIG. 10, pressure sensor 42 picks up a signal representative of the filling pressure of the left ventricle, which must be equal to 6 mm Hg, the duration of the cycle being then 630 milliseconds. A comparator 44 compares the signal representative of the effective filling pressure 48 of the left ventricle with a signal representative of said reference pressure: if the signal provided by comparator 44 established an equality no signal for adjusting the duration of the cycle is provided. If the filling pressure is greater than the reference filling pressure, a signal is provided at 46 for increasing proportionnaly the duration of the cycle. In the opposite case, a signal provided at 45 causes the duration of the cycle to be reduced proportionnally, the limit values of the duration of the cycle being 430 milliseconds–700 milliseconds.

Figure 11:
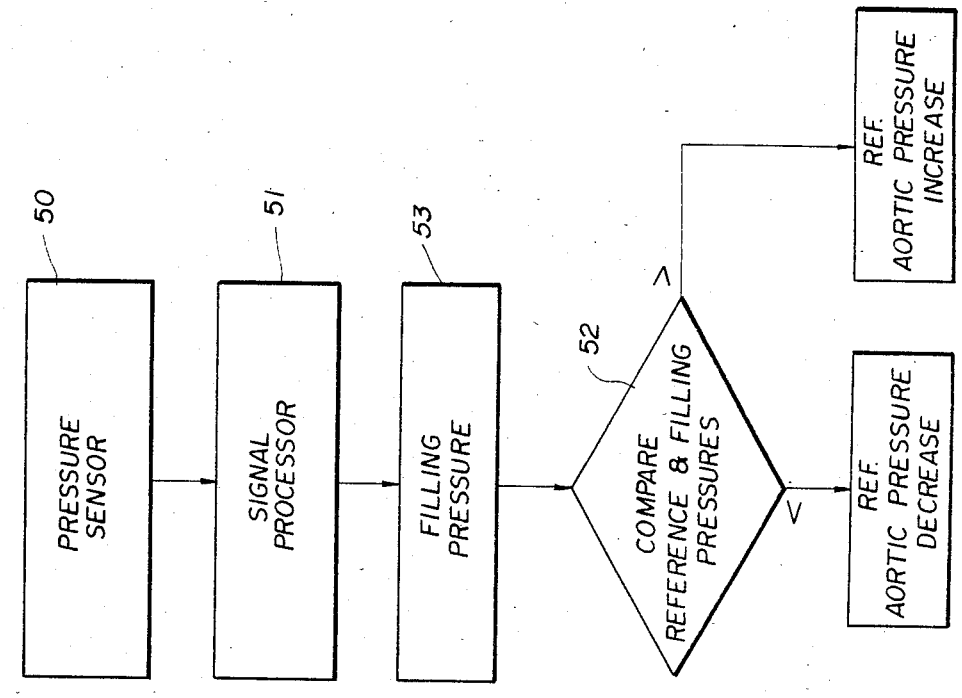
FIGS. 9, 10 and 11 are logic block diagrams of the servo-controls which provide regulation of cardiac flow in the prosthesis of the invention.

The third servo-control, such as shown in FIG. 11, is coupled to the first servo-control which, as was described above (in FIG. 9) establishes a relationship between, on the one hand, the activation pressure used on the pneumatic pressure distributor and the percentage of the pressurizing time and, on the other hand, a reference value of the predetermined mean aortic pressure.

This predetermined aortic pressure is that of the patient before implantation of the prosthesis, the patient being in a normal condition, i.e. having a constant circulating volume. Now, this volume cannot be considered as constant. In fact, during solid and especially liquid feeding, a part of the liquid ingested passes into the blood, thus increasing the total volume thereof. Now, the physiological mechanism is such that this increase in volume causes an increase in the arterial pressure which, by acting on the kidney, causes the renal hemodialysis which eliminates the surplus liquid in the blood and re-establishes the initial circulating volume.

To take into account this regulating function of the heart, the regulator device of the prosthesis must function to increase the aortic pressure when the circulating volume increases. The preset reference level of aortic pressure of the servo-control device must then be modified.

These variations in blood volume, which causes a variation in the filling pressure of the right ventricle, lead to measuring this filling pressure to compare it with a predetermined mean pressure which is approximately 0 mm Hg, the result of this comparison controlling the variation of the reference aortic pressure initially fixed at about 100 mm Hg.

Thus, the third servo-control of the invention comprises a sensor 50 for detecting the filling pressure of the right ventricle, for example a piezoelectric sensor placed in the right ventricular cavity of the prosthesis or a pressure sensor placed in an energy module connected by a tube to the right ventricular cavity of the prosthesis; this sensor 50 sends its output signal 53 to a comparator 52 to compare it with a reference for the filling pressure of the right ventricle, the outputs of the comparator controlling the aortic pressure reference.

So that an untimely and fleeting accidental variation of the filling pressure of the right ventricle does not influence the aortic pressure, the output signal of sensor 50 is fed to a processor 51 which only delivers a signal at the end of a predetermined period, an hour for example, this integrated signal being fed to comparator 52 to be compared with a corresponding reference signal.

The servo-controls of the invention act synergestically and are implemented by means of a microprocessor, so that the cardiac prosthesis of the invention responds, by appropriate flow variations, to the physiological variations of the resistances of the systemic vascular circuit, in order to bring the mean aortic pressure constantly back to its reference value, in the case where only the first two servo-controls are provided and to cause it to vary depending on the variation of the volume of the circulating blood, in the case where the device for regulating the cardiac flow also comprises the third servo-control of the invention; these servo-controls permit moreover the left ventricular filling pressure to be maintained within physiological limits.

The combination of means which characterizes the invention comprises: a sealed monoblock case whose form and spatial bulk substantially reproduce those of the natural heart; a sealed actuating device, included in said case and comprising a convex specific elastic membrane having a large area, working by elongation, whose actuation provides the volume displacements required in the right ventricle delimited by this membrane and the corresponding wall of the case, according to specific ways and means: an increase in the activation pressure from 150 to 250 mm Hg. causes a variation of the displaced volume from 80 to 150 ml; and a membrane working by deformation on each side of a plane of symmetry, whose deformations cause the volume displacements required in the left ventricle delimited by the second membrane and the corresponding part of the case; the activation of this actuating device by a single activation source or possibly by two activation pumps, in this latter case the openings of the right rigid support are closed; the disposition, in valvular orifices provided in the case and whose diameter is sufficiently great not to hinder the circulation, of valves whose passage section is sufficiently great to reduce as much as possible the transvalvular pressure drops; such a combination of means confers on the cardiac prosthesis of the present invention optimal dimensions having regard to its bulk, the absence of hindrance concerning the return circulation and the reduction to a minimum of the anatomical and functional dead spaces, while allowing it to operate at blood flows substantially greater than those provided by the cardiac prostheses known in the prior art. Thus, the overall volume of the prosthesis of the present invention does not exceed 400 cm$^3$, whereas it is capable of providing maximum flows reaching 16 liters/minute at a frequency of 140 cycles/minute, from a mean pressure of the left atrium of 15 mm Hg. The precise space taken up by the prostheses known in the prior art which include dead spaces is between 600 and 850 cm$^3$ and the maximum flows which they are capable of pumping are of the order of 12 to 14 liters, 14 liters being a maximum, at a frequency of 120 cycles/minute and at a mean left artrial pressure of 15 mm Hg. The space taken up by, and the performances of the cardiac prosthesis of the invention comply then perfectly, as shown above, to the anatomical and physiological constraints regard to which is a sine qua non condition of the success of implantation of a cardiac prosthesis. Because of its biventricular monoblock structure, the cardiac prosthesis of the invention is implanted like a heart graft.

To the abovementioned advantageous features are to be added the arrangements made for minimizing the risks of thrombogenesis, by suppression of the metal pieces in contact with the blood and by the choice of the materials used for forming the blood bladders 19 and 20 which isolate the blood circulation in the ventricular spaces 17 and 18 with respect to the actuating device and the case.

The bladders 19 and 20 could be made from specific polyurethanes, such as "BIOMER", "AVCOTHANE" or "PELLETHANE", and the like, as is known to those skilled in these arts.

Finally, one has to add to the abovementioned features, the arrangement of the regulating means which, in accordance with the invention allow the blood flows to be regulated in the cardiac prosthesis not only with respect to the filling pressures, which are upstream input pressures, but also with respect to the aortic and pulmonary pressures, which are downstream output pressures, thus allowing the blood flows in the prosthesis to be adapted to the variations of the pulmonary and systemic resistances. The activation pressure and the duration of the systole are regulated to a reference value of the mean aortic pressure and the duration of the activation cycle is regulated to the pressure of the left atrium, within time limit values of about 700 to 430 milliseconds. Since these two servo-controls act synergestically, they allow the prosthesis to respond to the variations of the pulmonary and systemic variations by power variations ("contractility"), which anticipate the increase in the central venous pressure and reproduce in that the flow adaptation mode of the homeometric-type described by SARNOFF.

It has to be understood that the size of the present new "low profile" total cardiac prosthesis depends on the subject. In the case of a man, the area of the membrane 4 which works by elongation is preferably about 98-105 cm$^2$. If the subject is a woman, the whole cardiac prosthesis size is homothetically reduced by about 15%. The homothetic reduction is about 25% if the subject is a child.

Implantation tests of cardiac prostheses of the abovementioned prior Art are at present in the experimental stage and are carried out exclusively on animals, and more particularly on calves, because of the fact that the pericardial cavity of these animals as well as the circulatory functional conditions, present substantially the same anatomical and functional constraints as those which prevail in human beings. At this experimental stage, the implantation of total cardiac prosthesis presents an interest of prime importance for the study of the cardio-circulatory system, for the physio-pathological study of cardiac insufficiency, of arterial hypertension, of acquired or congenital heart diseases, etc. On the other hand, the work in progress at present in the world all tends, on the one hand, to produce reliable total cardiac prostheses, adapted to efficiently replace the natural heart, causing neither infection of the pericardial cavity or of the tissues, nor internal formation of thrombosis and, on the other hand, to perfect activation devices which are either implantable or, if they are extracorporal, portable, so as to reduce to a minimum the dependence of the bearer of the prosthesis, the aim in view being to be able, by means of the reliable and usable "tool" perfected, to undertake clinical experiments on human beings with an initial object of provisional implantations, while waiting for a graft donor, and as a long-term objective, the more or less definitive implantation of cardiac prostheses whose efficiency, reliability, harmlessness and operating life will have been checked.

It is apparent that within the scope of the invention, modifications and different arrangements can be made other than is here disclosed. The present disclosure is merely illustrative with the invention comprehending all variations thereof.

I claim:

1. A total heart prosthesis comprising a case implantable in the pericardial cavity and constructed from a material biocompatible with respect to the surrounding tissues, aperture means for power fluid, and inlet and outlet blood valvular orifices opening into said case;
   a curved internal rigid support having a generally convex face and a generally concave face and dividing said case into a right ventricle chamber and a left ventricle chamber having substantially the same volume but different configurations, said right ventricle chamber being adjacent said convex face of said rigid support;
   a first blood bladder positioned freely within said right chamber with its lip sealed to one of said inlet and one of said outlet orifices;

a second blood bladder position freely within said left chamber with its lip sealed to another one of said inlet and another one of said outlet orifices;

first and second elastomeric membranes within said case, said first membrane being adapted to rest against said convex face of said rigid support, and said second membrane being capable of resting against said concave face of said rigid support;

a fluid energy source adapted to be connected to said aperture means for conducting said pressurized fluid flow onto said membranes for deforming said first membrane through elongation thereof and thereby varying the volume of said right chamber, and for displacing said second membrane to vary the volume of said second chamber, both said chambers thus forming a biventricular one-piece unit;

valves mounted in said valvular orifices for anastomosis with the blood vessels of the circulatory network of a bearer, which valves have a diameter compatible with the auriculo-ventricular natural aortic and pulmonary ejection characteristics of the blood vessels and with the physiological kinetic pressures of the blood circulating in the prosthesis from the left ventricle into the aorta and from the right ventricle into the pulmonary so as to minimize pressure drop phenomena and any transvalvular pressure gradient; and means for activating said fluid energy source, and means for regulating the cardiac flow with respect to the filling pressure of the left ventricle chamber and to the aortic pressure.

2. A total heart prosthesis according to claim 1, said first elastomeric membrane having a high degree of elasticity and a large surface area, said right chamber being so configured that in operation said first elastomeric membrane will stretch about 7–20%.

3. A total heart prosthesis according to claim 1 or claim 2 wherein said second elastomeric membrane is non-elastic, the volumes of each of said right and left chambers being no more than about 150 cm$^3$.

4. A total heart prosthesis according to claim 2 wherein said first elastomeric membrane has a high degree of stretchability of at least about 600% and a large surface area of about 80–110 cm$^2$, the volume displaced by stretching of said first elastic membrane away from the convex face of said rigid support being from 80–150 ml when subjected to 150–250 mmHg pressure variation.

5. A total heart prosthesis according to claim 1 comprising means to promote laminar blood flow toward the aorta without zones of zero speed blood flow, said means comprising a configuration of said right chamber such that in cross section it has a semi-crescent configuration which increases in width in three spatial dimensions from its tip to its base.

6. The cardiac prosthesis as claimed in claim 1, wherein said internal rigid support is pierced with a plurality of openings, in the case of mono-activated option.

7. A total heart prosthesis according to claim 1 or claim 2, wherein said means for activating said fluid energy source, and said means for regulating the cardiac flow comprise means to subject the right chamber to a physiological value of about −2 to +7 mmHg, and the left chamber to a physiological value of about +5 to +15 mmHg.

8. The cardiac prosthesis as claimed in claim 1, wherein the unit formed by the two said membranes and their support devices forms a sealed unit itself lodged in said sealed case, with which said unit is made integral by means of appropriate housings provided in said case to receive the ends of the two membranes and the ends of their respective supports.

9. The cardiac prosthesis as claimed in claim 1, wherein the distance between the membranes which delimit with the corresponding internal faces of the case, respectively the left chamber and the right chamber, increases in the three spatial dimensions from the top to the base of the prosthesis so as to orientate the speed vectors towards the corresponding output valvular orifice and to avoid any blood reticulation areas.

10. The cardiac prosthesis as claimed in claim 1, wherein each one of the valves mounted in the valvular orifices provided in the case is formed by a disk made from an appropriate hemocompatible material, whose diameter is substantially identical to that of the valvular orifice in which it is mounted.

11. The cardiac prosthesis as claimed in claim 1, wherein said case is equipped with inserts for anastomosis with the bearer of the prosthesis, which inserts are mounted in the valvular orifices provided in said case and are designed to receive securing means for which said valve is inserted.

12. The cardiac prosthesis as claimed in claim 1, wherein the means for activating the fluid energy source comprises an implantable electro-pneumatic or electro-hydraulic energy converter.

13. The cardiac prosthesis as claimed in claim 1, and means for supplying the fluid energy source comprising an electric motor from a nuclear energy source which are both implantable.

14. The cardiac prosthesis as claimed in claim 1, wherein means for supplying the fluid energy source are formed by an extracorporal pneumatic energy source connected to the cardiac prosthesis by means of a small-diameter transcutaneous tube, made from a material eliminating as much as possible the risks of transcutaneous infection.

15. The cardiac prosthesis as claimed in claim 14, wherein the pneumatic energy source is formed by two independent pumps acting respectively one on the elastic membrane of the right chamber, the other on the deformable membrane of the left chamber, the rigid support being pierced with one single opening for supplying gas, said single opening being connected to the corresponding pump by means of a tube.

16. The cardiac prosthesis as claimed in claim 15, wherein the first elastomeric membrane is a soft elastic membrane.

17. The cardiac prosthesis as claimed in claim 14, wherein said transcutaneous tube is coveered with reinhabitable tissue and equipped when mounted in the tissue with carbon pyrolyte disks which prevent shearing of the tube on the skin in the axial direction and avoid infection.

18. The cardiac prosthesis as claimed in claim 1, wherein the means for regulating the cardiac flow with respect on to the filling pressure of the left ventricle and to the aortic pressure, are associated with means for supplying said fluid energy source and comprise at least a dual servo-control which functions to adapt the blood flow in the cardiac prosthesis to variations of the pulmonary and systemic resistances by regulating the activation pressure and the percentage of systolic time in the cycle according to a reference value of the mean aortic pressure and by regulating the duration of the activation cycle according to the pressure of the left atrium, between limits ranging between 700 to 430 milliseconds.

19. A total heart prosthesis essentially formed by a biventricular monoblock unit formed by a sealed case implantable in the pericardial cavity and constructed from a material biocompatible with respect to the surrounding tissues and formed with valvular orifice, the blood circulating in the ventricles being isolated from the prosthesis, wherein the case comprises an actuating device formed by two elastomeric membranes one of which works by elongation and delimits with the corresponding internal face of the case a space which constitutes the right ventricle, and the second of which works by deformation and is mounted to determine a gap, or left ventricular space, between it and the corresponding internal face of the case;

means for isolating the external part of the prosthesis with respect to the blood circulating in the ventricular spaces of the prosthesis mounted respectively in association with the external face of the membrane which delimites the right ventricle and in association with the external face of the membrane which delimits the left ventricle;

valves mounted in the valvular orifices provided in the case for anastomosis with the vessels of the circulatory network, which valves have a diameter compatible with the auriculo-ventricular natural aortic and pulmonary rejection characteristics of the bearer's blood vessels and with the physiological kinetic pressures of the blood circulating in the prosthesis, from the left ventricle into the aorta, and from the right ventricle into the pulmonary, so as to avoid as much as possible pressure drop phenomena, and to reduce to a minimum the transvalvular pressure gradient;

means for activating a motor device associated with the prosthesis and which provides it with supply pressure substantially equivalent to the physiological values of the natural ventricular pressures, and means for regulating the cardiac flow with respect to the filling pressure of the left ventricle and to th aortic pressure;

wherein the means for regulating the cardiac flow with respect to the filling pressure of the left ventricle and to the aortic pressure, are associated with means for supplying the actuating device and comprise at least a dual servo-control which functions to adapt the blood flow in the cardiac prosthesis to variations of the pulmonary and systemic resistances by regulating the activation pressure and the percentage of systolic time in the cycle according to a reference value of the mean aortic pressure and by regulating the duration of the activation cycle according to the pressure of the left atrium, between limits ranging between 700 to 430 milliseconds;

wherein said means for regulating the cardiac flow comprise, in the case where they are associated with said activation means comprising a pneumatic energy source, a first servo-control which comprises a pressure reducer which causes the activation pressure to vary between 150 to 250 mm Hg, under the action of a signal supplied by a comparator, after comparison of a signal corresponding to the effective pressure of the bearer of the prosthesis with a signal corresponding to a reference pressure, for example 100 mm Hg, if the effective pressure differs from the reference pressure, to increase or reduce the activation pressure exerted on the membrane which forms the right ventricle and to increase or reduce correspondingly the flow in said right ventricle, and a second servo-control which uses the flow variations in the right ventricle and the resulting increase in the mean pressure of the left atrium which is represented by a pressure signal representative of the filling pressure of the left ventricle, supplied by a container associated with the pneumatic activator, for regulating the activation period between 700 to 430 milliseconds by means of a proportional signal provided following the establishment by a microprocessor, associated with said container of a proportional relationship between the filling pressure of the left ventricle and the period of the activation cycle.

20. The cardiac prosthesis as claimed in either one of claims 18 or 19, wherein said means for regulating the cardiac flow comprise a third servo-control for detection of the mean pressure of the right atrium and comparison of this pressure with a reference pressure, the result of this comparison controlling the value of the determined reference pressure with respect to the aortic pressure.

21. The cardiac prosthesis as claimed in claim 20, wherein mean right atrial pressure measured by the third servo-control are stored for a predetermined period of time and their mean value is compared with the value of the predetermined reference pressure to control the change in the predetermined value of the reference aortic pressure.

22. The cardiac prosthesis as claimed in claim 20, wherein the third servo-control comprises a right ventricle filling pressure sensor, said sensor supplying its output signal to an integrator or recorder whose output signal is applied to a comparator to be compared with a predetermined reference signal, this comparator controlling the aortic pressure reference signal of the comparator of the servo-control comparison to the aortic pressure of the first servo-control.

23. The cardiac prosthesis as claimed in claim 21, wherein the third servo-control comprises a right ventricle filling pressure sensor, said sensor supplying its output signal to an integrator or recorder whose output signal is applied to a comparator to be compared with a predetermined reference signal, this comparator controlling the aortic pressure reference signal of the comparator of the servo-control comparison to the aortic pressure of the first servo-control; and wherein said case has a small bulk of no more than 400 cm$^3$, large reserve volumes in each chamber of approximately 155 ml, and large intake valves of approximately 35 mm internal diameter.

24. The cardiac prosthesis as claimed in claim 1, wherein said rigid support is pierced with a single gas supply opening, in the case of bi-activated option.

25. A device for regulating the blood flow in a cardiac prosthesis of the type having a cycle by cycle fluid pressure activated right ventricle chamber and a fluid pressure activated left ventricle chamber, a fluid energy source, first sensor means whose output is representative of the aortic pressure, second sensor means whose output is representative of the left ventricle filling pressure, said device comprising first comparator means of the output of said first sensor means and of a reference aortic pressure value, second comparator means of the output of said second sensor means and a reference left ventricle filling pressure delivery thereof as well as the ratio of the systole time with respect to the cycle total time, and the output of said second comparator means being/connected to said fluid energy source to modify said cycle total time whereby the blood flow substantially obeys the homeometric SARNOFF's law.

26. The device for regulating the blood flow as claimed in claim 25, wherein a third sensor means is provided which causes the aortic pressure to vary depending on variations of the volume of circulating blood, which variations cause a variation in the filling pressure of the right ventricle whose measurement and comparison with a predetermined mean pressure control the variation of the reference level of aortic pressure of the first comparator means.

* * * * *